United States Patent
Plumb et al.

[11] Patent Number: 5,961,441
[45] Date of Patent: Oct. 5, 1999

[54] SURGICAL OTOSCOPE AND METHOD

[75] Inventors: Todd R. Plumb, 885 E. 200 North, Nephi; Denise Balls, Provo; Dale C. Dunn, Orem; Carlos Garrido, Springville; Matthew W. McClelland, Provo, all of Utah; Rodolfo Peña, Tapachula Chiapas, Mexico; W. Douglas Stout, Orem, Utah

[73] Assignee: Todd R. Plumb, Nephi, Utah

[21] Appl. No.: 08/661,648

[22] Filed: Jun. 11, 1996

[51] Int. Cl.⁶ ........................................................ A61B 1/22
[52] U.S. Cl. ............................................. 600/20; 600/104
[58] Field of Search .................................. 600/104, 200, 600/184, 221

[56] References Cited

U.S. PATENT DOCUMENTS

| | | | |
|---|---|---|---|
| 2,162,681 | 6/1939 | Ryan | 600/200 |
| 3,020,919 | 2/1962 | Chester | 600/200 |
| 5,363,839 | 11/1994 | Lankford | 600/200 |
| 5,390,663 | 2/1995 | Schaefer | 600/200 |
| 5,419,312 | 5/1995 | Arenberg et al. | 600/200 |

*Primary Examiner*—Jerome W. Donnelly
*Attorney, Agent, or Firm*—Trask, Britt & Rossa

[57] ABSTRACT

The present invention is directed to a surgical otoscope for examining and operating upon the external ear canal and tympanum. The surgical otoscope comprises an optical diagnostic instrument and an adapter member attached thereto. An image conveyer and a light transmitter are located within the optical-diagnostic instrument and extend therefrom and into the adapter member. The adapter member includes extendable and retractable surgical instrumentation and a suction tube. The combination of optical diagnostic and surgical instrumentation in the same device a enables a physician to simultaneously examine and operate upon the external ear canal and tympanum. Accordingly, the physician may selectively use the instruments while viewing the areas to be examined or operated upon through the same device.

13 Claims, 7 Drawing Sheets

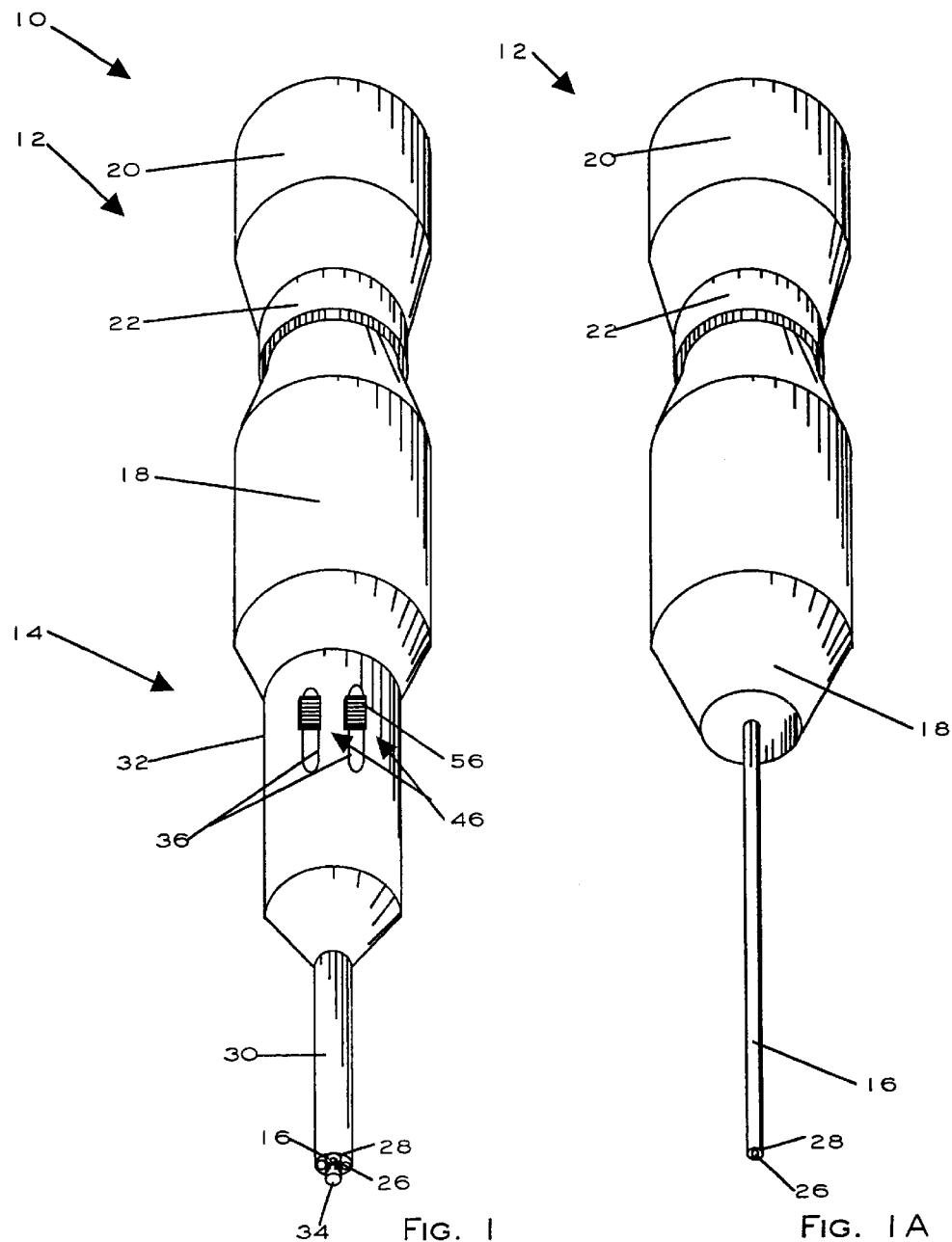

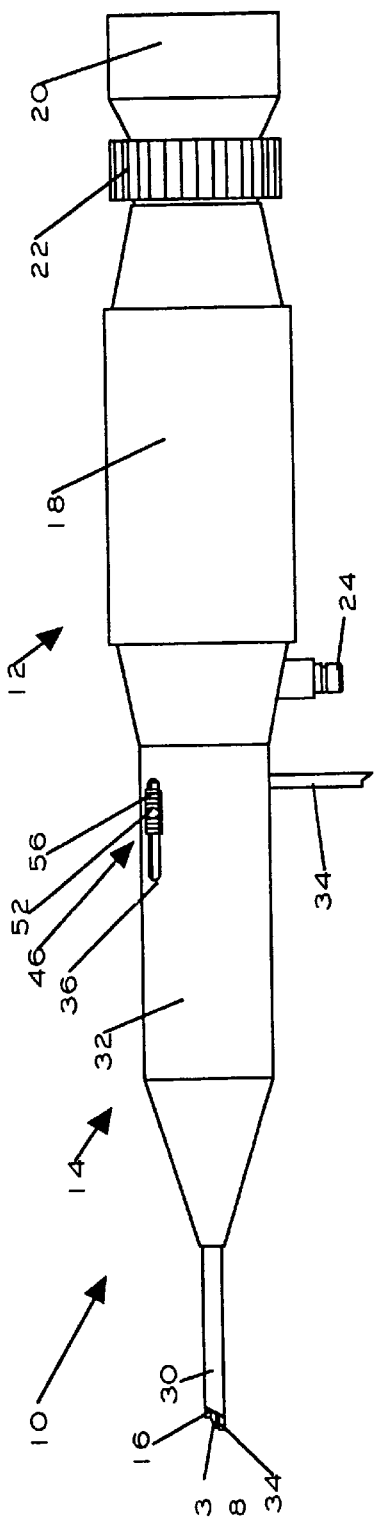
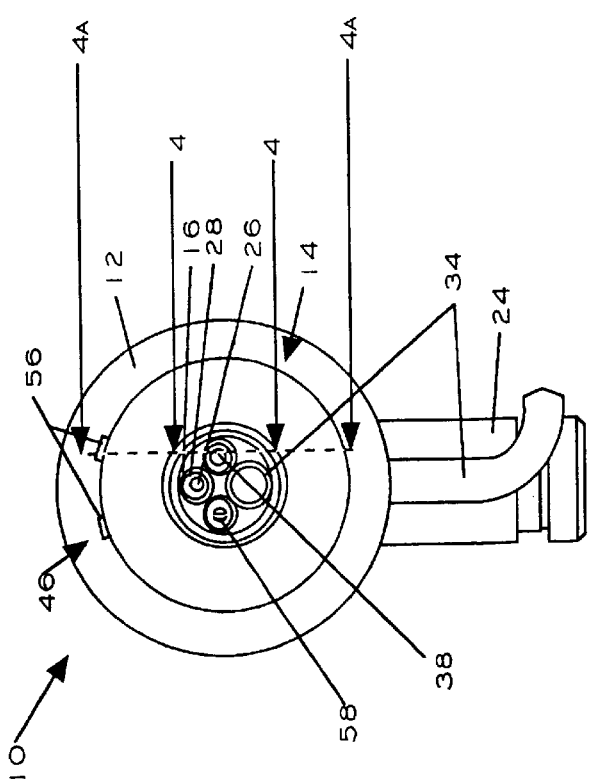
FIG. 2
FIG. 3

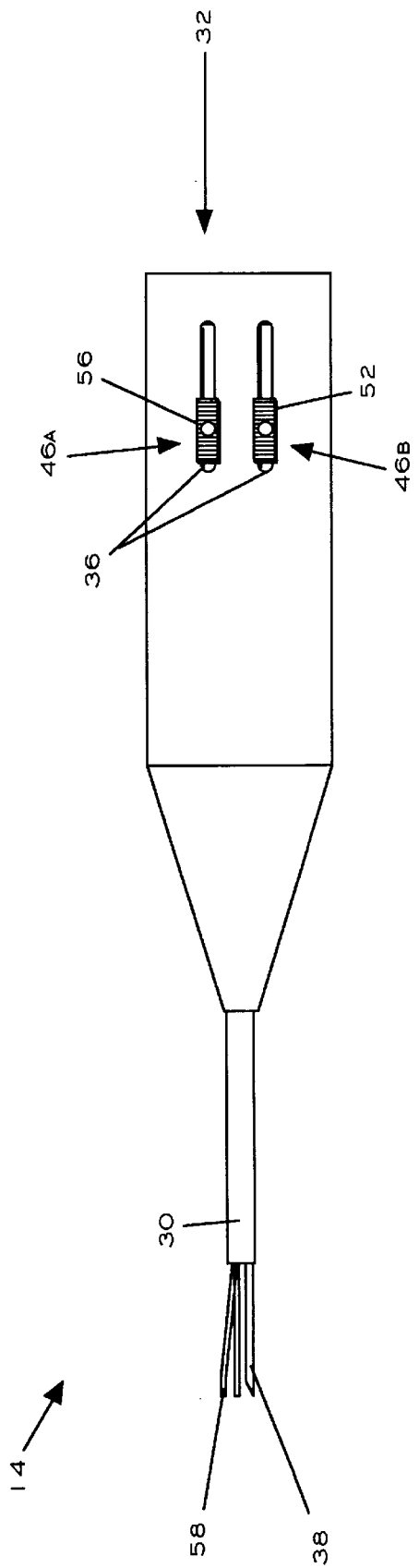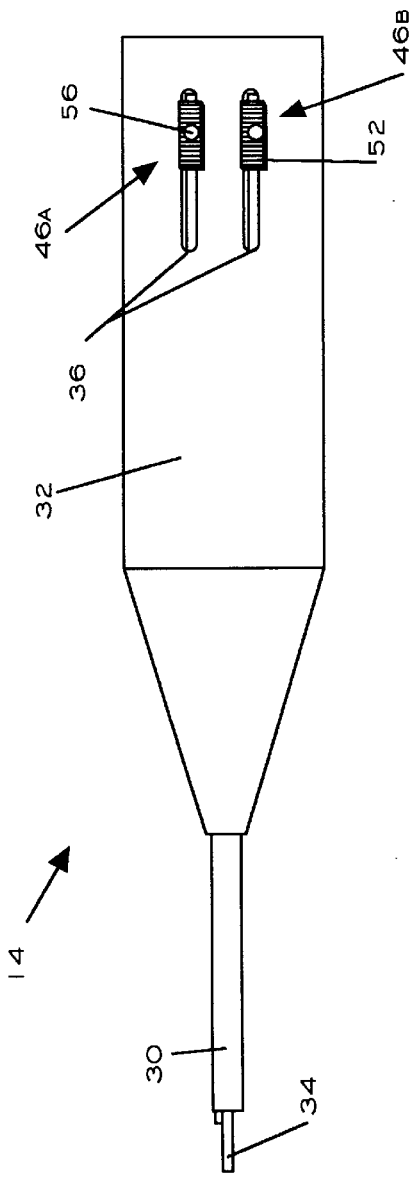
FIG. 5
FIG. 6

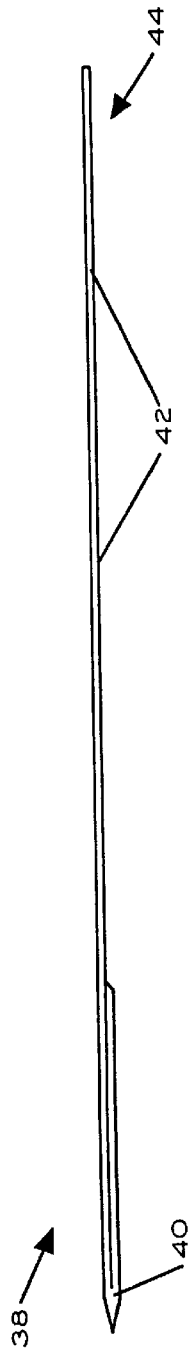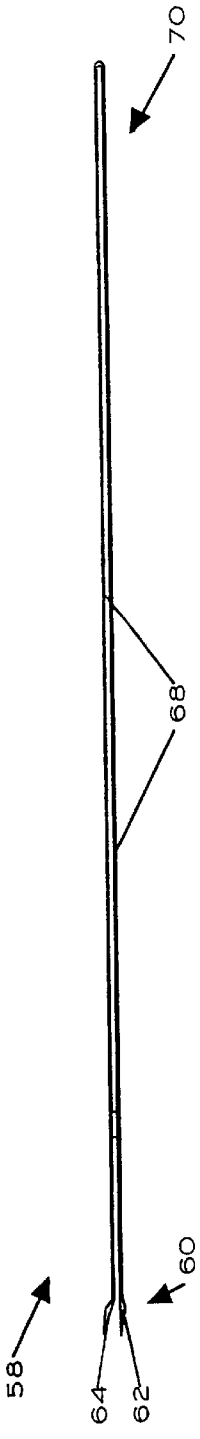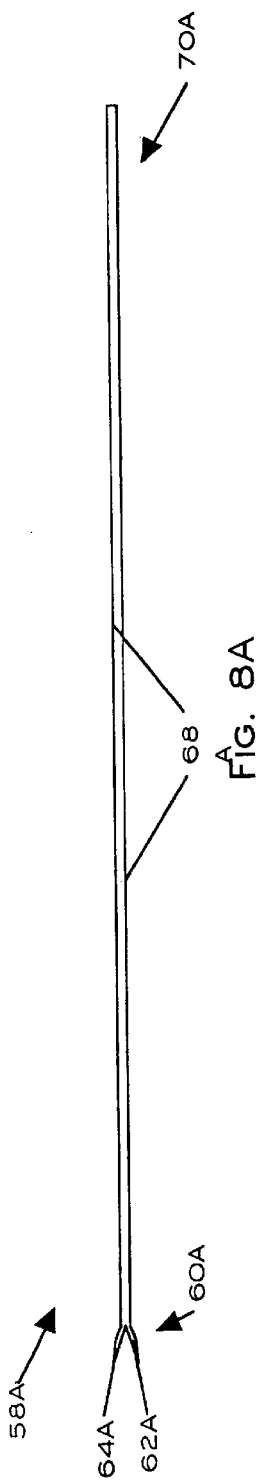

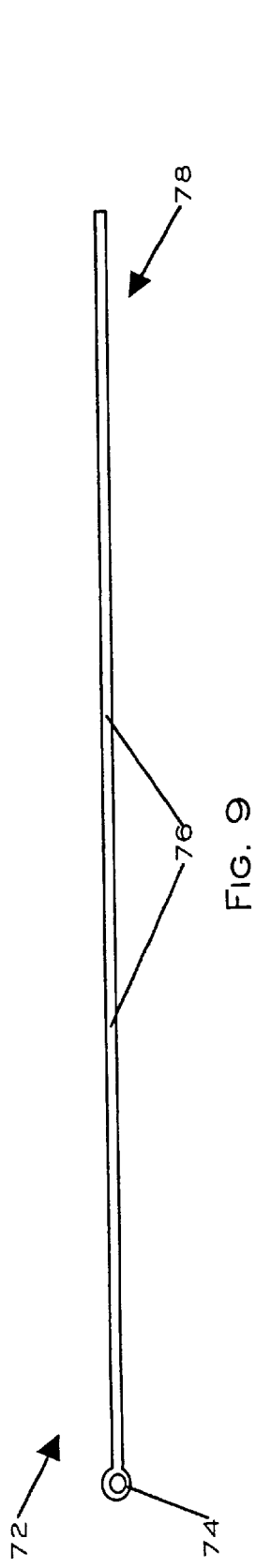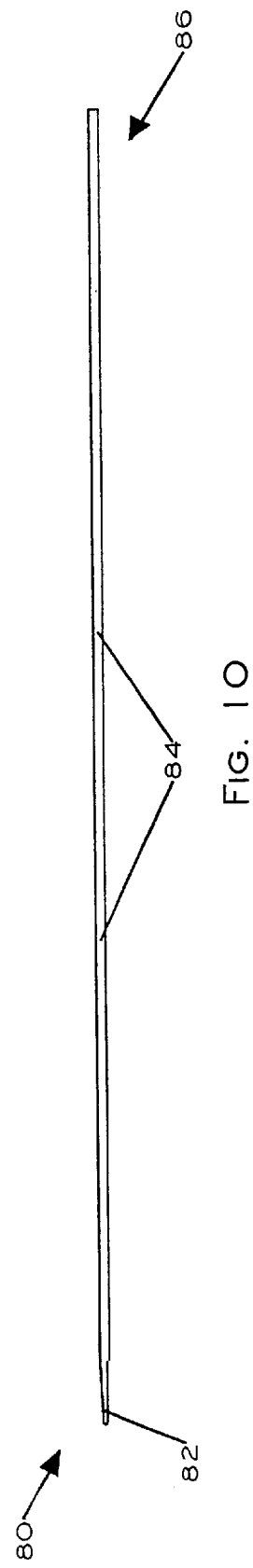

SURGICAL OTOSCOPE AND METHOD

BACKGROUND OF THE INVENTION

The present invention relates to otoscopes for use in examining and operating upon the external ear canal and the ear drum. More particularly, the present invention relates to an otoscope which combines visual diagnostic features with surgical instruction and a method for operating upon the external ear canal and the ear drum using the surgical otoscope.

Otoscopes are available in a wide variety of forms. An otoscope generally facilitates a physician's examination of a patient's external ear canal and ear drum. Typically, known otoscopes are used for examination purposes. For example, Welch Allyn, Inc. of Skananteles Falls, N.Y. manufactures a device which includes a light source and an optical lens or eye piece through which one may view the ear. Photographic or video cameras attach to the eye pieces of many known otoscopes. Otoscopes are commonly employed for observation during surgery and other treatment of the external ear canal and ear drum. However, none of the existing otoscopes include surgical instrumentation. In order to treat the external ear canal or conduct surgical procedures such as myringotomy, a physician must work around the otoscope. Thus, the physician's view is frequently disturbed or obstructed during the course of the procedure.

Some otoscopes, such as the Video Otoscope, U.S. Pat. No. 5,363,839 own ed by JEDMED Instrument Company of St. Louis, Mo. have a speculum, which is insertable into the ear canal for retracting or dilating the ear canal wall, and a pneumatic insufflator bulb, which forces air through the speculum and against the ear drum in order to demonstrate ear drum mobility.

One prior art otoscope is described in U.S. Pat. No. 4,785,796, by Philip D. Mattson of El Cajon, Calif. The apparatus is an otoscope capable of being coupled to a curette, which introduces fluids into and withdraws matter from small cavities such as the external ear canal. The curette of that device mounts to the otoscope in a stationary fashion. Therefore, the utility of that otoscope is very limited.

Another prior art otoscope is disclosed in U.S. Pat. No. 5,254,120, by James Z. Cinberg of South Orange, N.J. and Peter J. Wilk of New York, N.Y. That disposable otoscope includes an opening for insertion of examining and surgical instruments into a patient's ear canal. The instruments used with that otoscope are not part of the otoscope.

A surgical otoscope is needed which can be used for examination of the external ear canal and ear drum and for surgery thereon. More particularly, what is needed is a surgical otoscope which provides for manipulation of the visual and instrument components as a unit, stabilization of the instruments within the otoscope, extension and retraction of instruments from the otoscope, operation of the instruments using the same hand that holds the otoscope and reduced obstruction of the physician's view of the exteraal ear canal and ear drum as the instruments are used.

SUMMARY OF THE INVENTION

The present invention comprises a surgical otoscope which addresses the foregoing needs. The otoscope includes instruments used in surgery and treatment. The otoscope device of the present invention includes extendable and retractable instruments which are operated using the same hand that holds the otoscope. In addition, use of the instruments causes minimal obstruction of the physician's view through the otoscope.

A preferred embodiment of the invention includes an adapter member having extendable and retractable instruments, a light source and a means for image transmission therein. The adapter member attaches to an optical body having the light source and the means for image transmission therein. The light source connects to a power supply connector and the means for image transmission connects to a means for viewing.

Another preferred embodiment includes an adapter member with a port for insertion of additional existing instruments. A preferred method of using the present invention comprises introduction of the adapter member into the patient's external ear canal, visual examination of the area to be treated, extension, operation and retraction of surgical instruments and removal of the otoscope from the patient's ear. Further advantages of the present invention will become apparent from a consideration of the drawings and the ensuing description.

DRAWING FIGURES

FIG. 1 is an oblique top view of a preferred embodiment of the present invention, with the instruments retracted;

FIG. 1A is an oblique top view of the embodiment shown in FIG. 1, showing only a borescope portion;

FIG. 2 is a side plan view of the embodiment shown in FIG. 1, with one of the instruments partially extended;

FIG. 3 is a frontal plan view of the embodiment shown in FIG. 1;

FIG. 4A is a side cross section view of FIG. 3, through line 4A—4A of the adapter member;

FIG. 5 is a top plan view of the adapter member of the embodiment shown in FIG. 1, with the instruments fullly extended;

FIG. 6 is a top plan view of the adapter member of the embodiment shown in FIG. 1, with the instruments retracted;

FIG. 7 is a side plan view of a knife embodiment of the instrument of the embodiment shown in FIG. 1;

FIG. 8 is a top plan view of a clamp embodiment of the instrument of the embodiment shown in FIG. 1;

FIG. 8A is a top plan view of another clamp embodiment of the instrument of the embodiment shown in FIG. 1;

FIG. 9 is a top plan view of a curette embodiment of the instrument of the embodiment shown in FIG. 1;

FIG. 10 is a top plan view of a probe embodiment of the instrument of the embodiment shown in FIG. 1.

DETAILED DESCRIPTION OF THE PREFERRED EMBODIMENT

The present invention is directed to a hand-held surgical otoscope. The otoscope of the present invention includes first an optical body having a means for image transmission, a light source and a means for viewing, and second a surgical adapter member including surgical instrumentation attached to the optical body. This otoscope is especially useful for unobstructed visualization of the external ear canal and tympanum while performing medical procedures thereon. For example, one use of the otoscope of the present invention is to visualize the ear drum while using the same instrument to perform myringotomy thereon and insert an ear tube therein.

In this description, the preferred embodiment includes an optical body member connected to a surgical adapter member. The surgical adapter member has an insertion tube through which pass a means for image transmission, a fiber optic light guide, and surgical instrumentation. The fiber optic light guide emits light through the insertion tube. Similarly, the means for image transmission receives images from the insertion tube of the adapter member. Surgical instrumentation located within the adapter member extend from and retract into the adapter member through the insertion tube.

Figure 1B:
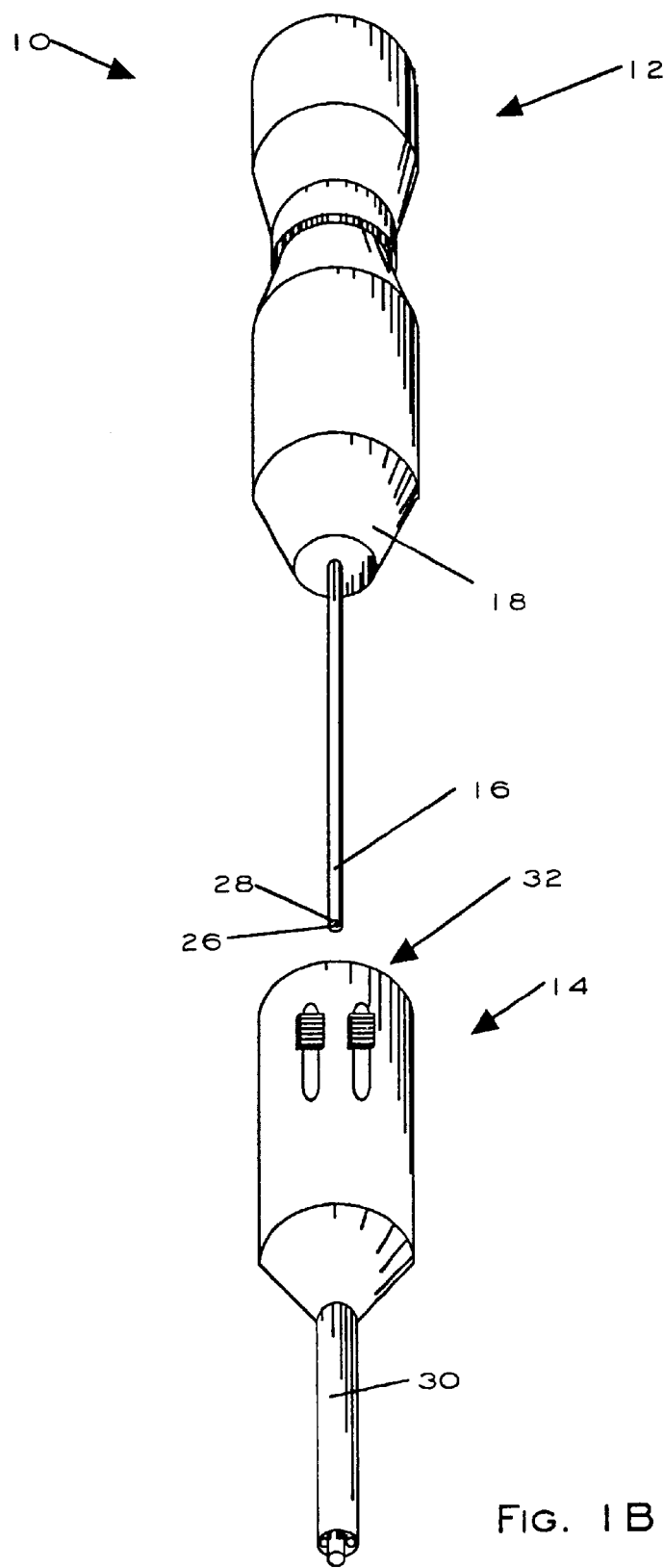
FIG. 1B is an exploded oblique top view of the embodiment shown in FIG. 1, demonstrating the extension of the rod lens and light source from the borescope into the adapter member.

Referring to FIGS. 1, 1A and 1B, the hand-held surgical otoscope 10 of the present invention includes an optical body 12 and a surgical adapter member 14. Optical body 12 and adapter member 14 are preferably made of stainless steel but can be manufactured from a variety of materials, including metals, plastics and vinyls. Preferably, the optical body and adapter member material will withstand various sterilization techniques.

As shown in FIG. 1A, optical body 12 is preferably a conventional borescope such as that manufactured by Instrument Technologies, Inc. of Westfield, Mass., which is typically used for looking into small areas in industrial applications. Optical body 12 includes a long hollow rod referred to as the image receiving tube 16 having an outer diameter of 2.0 mm or less, and a larger cylindrical member referred to as the image transmitting cylinder 18. An eyepiece 20 is located at image transmitting cylinder 18. Preferably, the eyepiece has a means for focusing 22 thereon.

Adapter member 14 is preferably substantially cylindrical in shape and has an extended insertion tube 30 and an optical body receiving end 32. Body receiving end 32 is fixedly attached to image receiving tube 16 of optical body 12. The outer diameter of insertion tube 30 facilitates insertion of the tube into a patient's external ear canal. Preferably, insertion tube 30 has an outer diameter of less than 3.0 mm.

As seen in FIGS. 2 and 3, a light guide adapter 24 is preferably located on the bottom of optical body 12. FIG. 3 shows that optical body 12 also has a rod lens 26 and a light guide 28, which pass through and extend from the optical body. With reference to FIG. 2, rod lens 26 conveys images from image receiving tube 16 to image transmitting cylinder 18. In the preferred embodiment, rod lens 26 has an outer diameter of 1.0 mm. Light guide 28 is preferably a fiber optic cable which conveys light projected into light guide adapter 24 to image receiving tube 16.

Adapter member 14 receives image receiving tube 16 which contains the portions of rod lens 26 and light guide 28 which extend from optical body 12. Rod lens 26 and light guide 28 extend into adapter member 14 at body receiving end 32 and through the adapter member to insertion tube 30, through which light guide 28 directs light and rod lens 26 receives images.

Adapter member 14 also includes a suction tube 34 and surgical instruments which extend through the surgical adapter member. Adapter member 14 also has access notches 36 formed therethrough. Preferably, suction tube 34 passes through the bottom of adapter member 14, facilitating the attachment of otoscope 10 to a vacuum source (not shown). As seen in FIG. 4A, access notches 36 are preferably formed through the top of adapter member 14.

Figure 4:
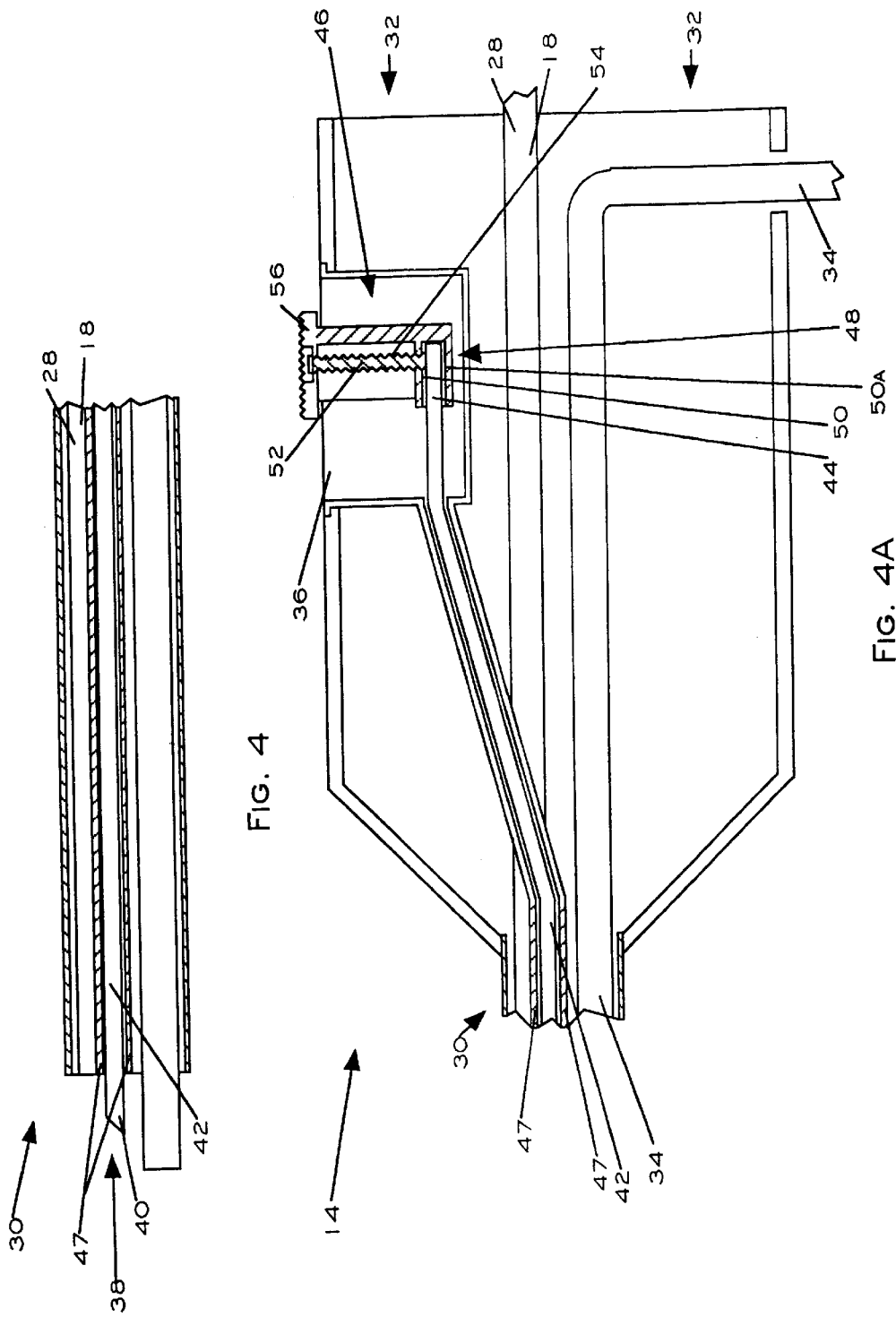
FIG. 4 is a side cross section view of FIG. 3, through line 4—4 of the functional end of the adapter member.

As illustrated by FIGS. 4 and 4A, each surgical instrument has an operative portion located at one end of a shaft, and a slider 46 located at the other end, a control end, of the shaft. The shaft is preferably contained within a guide tube 47. The operative portion of each surgical instrument is located at insertion tube 30. Slider 46 has a finger control portion 56 which passes through access notch 36 and is preferably slidingly attached thereto.

In the preferred embodiment of otoscope 10, adapter member 14 contains two surgical instruments. Preferably, slider 46 further comprises a shaft receiving portion 48, which removably engages the control end of a surgical instrument shaft. Shaft receiving portion 48 is preferably tubular, having an inner surface 50. When control end 44 is placed within shaft receiving portion 48, the shaft is held securely into place by set screw 52, which screws into and through a threaded bore 54 formed through slider 46 from finger control portion 56 to the upper inner surface 50 of the shaft receiving portion and secures the control end of shaft 42 against the opposing inner surface 50A of the shaft receiving portion.

As demonstrated in FIG. 5, when finger control portion 56 of slider 46 is positioned along the end of access notch 36 closest to insertion tube 30, the surgical instrument is fully extended. FIG. 6 shows that as finger control portion 56 is moved along access notch 36 toward optical body 12, the surgical instrument retracts into insertion tube 30.

The various embodiments of the surgical instrument include a knife 38, a clamp 58, a curette 72 and a probe 80, shown in FIGS. 7, 8, 9 and 10, respectively. As illustrated in FIGS. 3 and 5, otoscope 10 preferably has clamp 58 and knife 38.

FIG. 7 shows knife 38, which has a cutting end 40 at one end of a shaft 42 and a control end 44 at the other end of the shaft. Cutting end 40 is fixedly attached to shaft 42. Shaft 42 attaches to slider 46, as shown in FIG. 4A.

Referring to FIG. 8, clamp 58 has a clamping end 60 and a control end 70 at opposite ends of a shaft 68. Shaft 68 includes two thin wires fixedly attached to each other near clamping end 60 and near control end 70. Clamping end 60 has a stationary arm 62 and a retractable arm 64. Retractable arm 64 is a tension spring which is bent away from stationary arm 62. In its retracted position within guide tube 47, stationary arm 62 and retractable arm 64 are forced together. As clamp 58 is extended from adapter member 14 and out of guide tube 47, the spring tension of retractable arm 64 forces it away from stationary arm 62. Thus, extension of clamp 58 from adapter member 14 opens the clamp. As clamp 58 is retracted into guide tube 47, the guide tube forces retractable arm 64 toward stationary arm 62, closing the clamp. Thus, as clamp 58 is retracted, it closes, and the clamp is completely closed when fully retracted.

With reference to FIG. 8A, another embodiment 58A of the clamp has two movable spring loaded arms 62A and 64A at clamping end 60A. Shaft 68A is a single thin rod. Arms 62A and 64A are forced together when retracted within guide tube 47, which is shown in FIG. 6. As clamp 58A is extended from adapter member 14 and out of guide tube 47, the spring forces arms 62A and 64A away from each other. Thus, extension of clamp 58A from adapter member 14 opens the clamp. As clamp 58A is retracted into guide tube 47, the guide tube forces arms 62A and 64A toward each other, closing the clamp. Thus, as clamp 58A is retracted, it closes, and the clamp is completely closed when fuilly retracted.

Other embodiments of the clamp are similar to biopsy forceps, such as those manufactured by Olympus Corporation, of Lake Success, N.Y.

FIG. 9 illustrates curette 72, which has a long, cylindrical shaft 76 with an operative loop 74 fixedly attached to one end. The other end of shaft 76 is a control end 78, which is removably engaged by shaft receiving portion 48 of slider 46.

FIG. 10 shows probe 80, which comprises a long, cylindrical shaft 84 having an operative tip 82 fixedly attached to one end. The other end of shaft 84 is a control end 86, which is removably engaged by shaft receiving portion 48 of slider 46.

Myringotomy and ear tube insertion provides an example of the use and operation of the best mode of the otoscope of the present invention. With reference to FIGS. 5 and 6, a physician moves clamp slider 46A toward insertion tube 30 to open clamp 58. An ear tube is positioned between arms 62 and 64 of clamp 58. Clamp slider 46A is then moved away from insertion tube 30 until the ear tube is secured between arms 62 and 64. Next, the tip of insertion tube 30 of otoscope 10 is inserted into a patient's ear. At this point, the physician examines the patient's eardrum, determines the area upon which the myringotomy will be performed and positions otoscope 10 accordingly. Knife slider 46B is then moved toward insertion tube 30, extending knife 38 to incise the patient's ear drum. Next, knife 38 is completely retracted by moving knife slider 46B away from insertion tube 30. A vacuum source is then activated, facilitating the removal of blood, pus and debris through suction tube 34. The physician positions otoscope 10 to insert the ear tube into the incision. Clamp slider 46A is then moved toward insertion tube 30 to open clamp 58 and release the ear tube. Finally, clamp 58 is retracted and otoscope 10 is removed from the patient's ear.

Referring now to FIGS. 4 and 4A, the placement of knife 38 within surgical adapter member 14 provides an example of the replacement and securing of surgical instruments in the adapter member. First, slider 46 is moved in a forward position, toward insertion tube 30, extending the surgical instrument from the insertion tube. Set screw 52 is then loosened in order to release the control end of a surgical instrument which is presently placed in adapter member 14. The surgical instrument is then removed from shaft receiving portion 48 and guide tube 47 by pulling the surgical instrument from the tube. Next, control end 44 of knife 38 is inserted into adapter member 14 through guide tube 47. Shaft 42 is passed through guide tube 47 until control end 44 enters access notch 36. Maintaining the forward position of slider 46, control end 44 slides into shaft receiving portion 48. Set screw 52 is then tightened, securing control end 44 against surface 50A.

Removal of wax or foreign bodies from the external ear canal provides an example of the use of the curette. Referring to FIGS. 4, 4A and 9, knife 38 is removed from surgical adapter member 14. Curette 72 is then inserted into and secured within adapter member 14. Both instruments are retracted. A physician then inserts the tip of insertion tube 30 into a patient's ear. At this point, the physician examines the patient's ear canal, determines the areas from which wax or foreign bodies must be removed and positions the otoscope accordingly. Curette 72 is extended and the wax or foreign body is loosened from the ear canal with operative loop 74. The wax or foreign body is then removed either through the suction tube by activation of a vacuum source or by use of the clamp. Finally, the surgical instruments are retracted and the otoscope is removed from the patient's ear.

Repositioning of an improperly situated ear tube within an ear drum provides an example of the use of the probe. With reference to FIGS. 4, 4A and 10, knife 38 is removed from surgical adapter member 14. Probe 80 is then inserted into and secured within adapter member 14. The surgical instruments are then retracted. A physician then inserts the tip of insertion member 30 into a patient's ear. Next, the physician examines the patient's ear drum, locates the improperly positioned ear tube and positions the otoscope accordingly. Referring to FIG. 10, probe 80 is then extended, and operative tip 82 is used to position the ear tube properly. Finally, probe 80 is retracted and the otoscope is removed from the patient's ear.

Although the description contains many specificities, these should not be construed as limiting the scope of the invention, but as merely providing illustrations of some of the presently preferred embodiments of this invention. For example, the otoscope described illustrates an otoscope having an eye piece for viewing images, a rod lens, a fiber optic light guide, two surgical instruments, and finger controls located at the top of the otoscope. However, different combinations of these features and several more embodiments of each feature are readily conceivable. For example, one could view images on video or the otoscope could have any number of instruments attached thereto. Likewise, the elements of the surgical otoscope may be constructed from any material that will fulfill the stated purpose and retain the functionality of each element.

Thus, the scope of the invention should be determined by the appended claims and their legal equivalents, rather than by the examples given.

What is claimed is:

1. A hand-held surgical otoscope comprising a hollow tubular member, at least one surgical instrument extendable therethrough, an actuation element positioned on the hollow tubular member and operably connected to the surgical instrument, an image transmission component extendable substantially through the length of the hollow tubular member, and a light communication component extendable substantially through the length of the hollow tubular member.

2. The hand-held surgical otoscope of claim 1, wherein the surgical instrument is extendable from and retractable into the hollow tubular member.

3. The hand-held surgical otoscope of claim 1, wherein the hollow tubular member comprises an insertion tube extending therefrom which is insertable into an external ear canal.

4. The hand-held surgical otoscope of claim 3, wherein the hollow tubular member includes a debris removal component.

5. The hand-held surgical otoscope of claim 3, wherein the image transmission component includes a direct view optical pathway through the hollow tubular member and extending into an optical body member.

6. The hand-held surgical otoscope of claim 3, wherein the light communication component comprises a fiber optic element.

7. A hand-held surgical otoscope comprising:
- an optical body member having an image transmission component and a light communication component which extend from the optical body member;
- a hollow adapter member attached to the optical body member and including an insertion tube extending therefrom, a suction tube, a plurality of instruments extendable from and retractable into the insertion tube, the image transmission component and the light communication component extending from the optical body member and through the insertion tube; and
- at least one actuation element operably connected to one of the instruments and positioned on the adapter member.

8. The hand-held otoscope of claim 7, wherein the image transmission component includes a direct view optical pathway through the insertion tube extending into the optical body member to the image transmission component.

9. The hand-held otoscope of claim 7, wherein the light communication component comprises a fiber optic element.

10. The hand-held otoscope of claim 9, wherein one of the instruments comprises a clamp element.

11. The hand-held otoscope of claim 9, wherein one of the instruments comprises a cutting element.

12. The hand-held otoscope of claim 9, wherein one of the instruments comprises a curette.

13. The hand-held otoscope of claim 7, wherein one of the instruments comprises a probe.

* * * * *